US009192784B1

(12) United States Patent
Ritt et al.

(10) Patent No.: US 9,192,784 B1
(45) Date of Patent: Nov. 24, 2015

(54) RADIATION DELIVERY ISOCENTER ANALYSIS TOOL

(71) Applicant: Radiological Imaging Technology, Inc., Colorado Springs, CO (US)

(72) Inventors: Daniel Ritt, Colorado Springs, CO (US); Charles Clements, Colorado Springs, CO (US); Ryan Young, Colorado Springs, CO (US)

(73) Assignee: Radiological Imaging Technology, Inc., Colorado Springs, CO (US)

( * ) Notice: Subject to any disclaimer, the term of this patent is extended or adjusted under 35 U.S.C. 154(b) by 0 days.

(21) Appl. No.: 14/740,774

(22) Filed: Jun. 16, 2015

(51) Int. Cl.
*A61N 5/10* (2006.01)
*G06T 11/00* (2006.01)

(52) U.S. Cl.
CPC ............ *A61N 5/1039* (2013.01); *A61N 5/1081* (2013.01); *G06T 11/005* (2013.01); *G06T 2210/41* (2013.01)

(58) Field of Classification Search
CPC .. A61N 5/1039; A61N 5/1081; G06T 11/005; G06T 2210/41
See application file for complete search history.

(56) References Cited

U.S. PATENT DOCUMENTS

2015/0093011 A1* 4/2015 Gaudio ................ G06T 7/0012
382/132

OTHER PUBLICATIONS

Low, Daniel A. et al; Minimization of target positioning error in accelerator-based radiosurgery; Med. Phys. 22 (4), Apr. 1995; pp. 443-448; American Association of Physicists in Medicine; http://dx.doi.org/10.1118/1.597475.
Brill, A. B. et al; American National Standard Procedures for Periodic Inspection of Cobalt-60 and Cesium-137 Teletherapy Equipment; ANSI N449.1-1978; Secretariat for N44; Published by Institute of Electrical and Electronics Engineers, Inc., New York, NY.
Kutcher, Gerald J. et al; Comprehensive QA for Radiation Oncology; American Association of Physicists in Medicine Report No. 46; Reprinted from Medical Physics, vol. 21, Issue 4, 1994; Published by American Institute of Physics.
Nath, Ravinder et al; AAPM Code of Practice for Radiotherapy Accelerators; American Association of Physicists in Medicine Report No. 47; Reprinted from Medical Physics, vol. 21, Issue 7, Jul. 1994; Sep. 1994; Published by American Institute of Physics.
Klein, Eric E. et al; Task Group 142 report: Quality assurance of medical accelerators; Med. Phys. 36 (9), Sep. 2009; Published Aug. 17, 2009 by American Association of Physicists in Medicine.
Lutz, Wendell et al; A System for Stereotactic Radiosurgery with a Linear Accelerator; Int. J. Radiation Oncology Biol. Phys., vol. 14, pp. 373-381; 1988 Pergamon Journals Ltd.

* cited by examiner

*Primary Examiner* — Mark R Gaworecki
(74) *Attorney, Agent, or Firm* — Bejin Bieneman PLC

(57) ABSTRACT

Each image in a first set of images includes respective exposures of an image capture device to a beam of radiation, each of a plurality of components of a radiation delivery system being at respective specified orientations with respect to a three-dimensional coordinate system during each of the exposures. Respective beam images are reconstructed from each of the exposures by drawing a line at a predetermined angle to the first image and through a center of a radiation beam shown on each first image. The reconstructed beam images are combined on a second image.

22 Claims, 13 Drawing Sheets

RADIATION DELIVERY ISOCENTER ANALYSIS TOOL

BACKGROUND

"Star Shots" (also called "spoke shots") are used for quality assurance in radiation therapy systems. Such images are so named because they feature images of radiation beams that generally form a star or spoke pattern. Star shots are typically obtained on film placed parallel to a radiation beam (for a gantry star shot) or perpendicular to the beam (for couch, primary collimator, or MLC star shots). A star shot may be used to determine the radiation isocenter location (i.e., center of rotation) for components of a radiation delivery system, e.g., a gantry, couch, primary collimator, and MLC (multi-leaf collimator) relating to a radiation device such as a linear accelerator, a Cobalt-60 unit, a Radiation Therapy simulator, etc. Accordingly, a goal of the star shot is to ensure that the center of rotation of the element of the radiation delivery system (gantry, couch, primary collimator, or MIX) is within a certain specification during normal rotational operation, thereby ensuring that the beam of radiation hits its intended target when delivered from different angles.

Obtaining desired precision can be particularly challenging, especially in the case of a linear accelerator gantry weighing several tons, and where the typical requirement for a standard linear accelerator gantry is that the beams must intersect within a circle of two millimeters (mm) in diameter, and less than one mm for linear accelerators capable of performing stereotactic treatments. Compounding the difficulty is that, in addition to the size of the radiation beam intersection circle being within tolerance, it is also a requirement that the location of the beam intersection center be within 1 mm of the mechanical isocenter of the radiation delivery system for all mechanical motion in the system, including motion of the gantry, couch, primary collimator, and/or MLC collimator rotations.

Present systems for obtaining a star shot to determine radiation isocenters typically depend on use of film, which is difficult to use, expensive, and increasingly difficult to obtain. Further, present systems for obtaining a star shot do not provide information relating to the mechanical isocenter of a system unless the mechanical isocenter is manually labeled, which is inefficient and prone to error.

DESCRIPTION

Introduction

Figure 1:
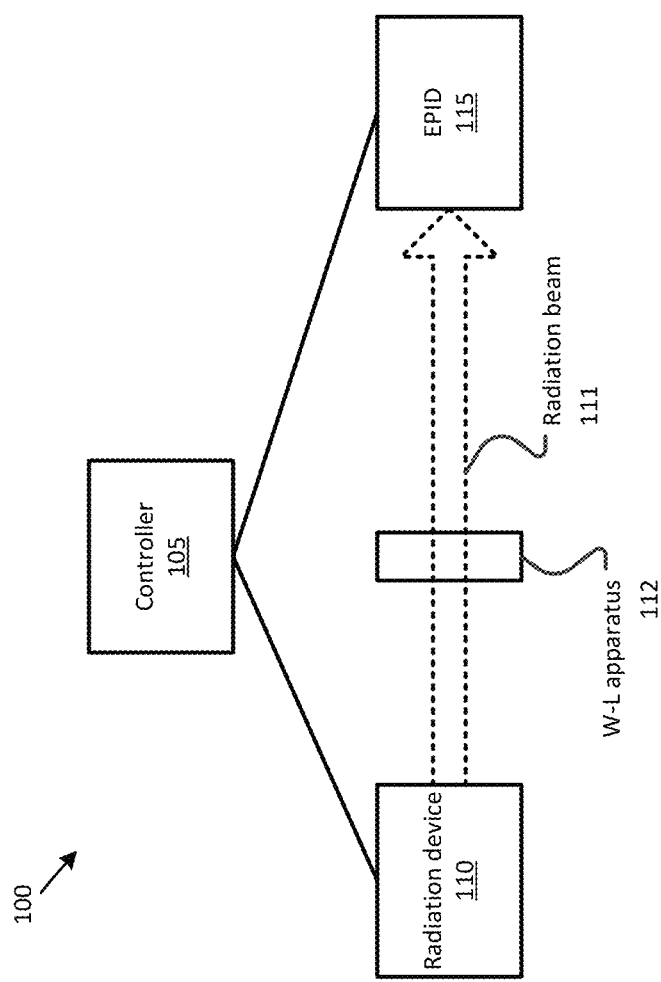
FIG. 1 is a block diagram of an example radiation delivery system.

As illustrated in FIGS. 1 and 2A-2F, a radiation delivery system 100 includes a test computer 105 programmed to determine tolerances with which a radiation device 110 can deliver radiation with respect to both radiation and mechanical isocenters of the system 100. A mechanical isocenter may be defined as a point where, under ideal conditions, gantry 125, collimator 130, and patient couch 120 rotation axes would intersect (i.e., the X, Y, and Z axes shown in FIGS. 2A-2F). A radiation isocenter may be defined as a point in space where, under ideal conditions, radiation beams 111 would intersect at all rotations of gantry 125, collimator 130, and/or patient couch 120. For accurate treatment by a radiation device 110, it is desirable to minimize actual deviations, i.e., to conform to the lowest tolerance possible but certainly to be below a threshold tolerance, with respect to the mechanical and radiation isocenters. The present system 100 provides for generating a synthetic star shot as disclosed herein, and thus provides a greatly improved mechanism for evaluating mechanical and radiation isocenters, deviations therefrom, and whether the radiation device 110 is delivering beams 111 within acceptable tolerances thereof.

For example, the computer 105 may generate a digital image, referred to herein as a synthetic star shot, that can be used to determine whether a radiation device 110 is able to deliver radiation within acceptable tolerances of both radiation and mechanical isocenters. The computer 105 obtains data for generating the digital image by directing a radiation beam 111 toward a Winston-Lutz test apparatus 112, which is known. Further as is known, an electronic portal imaging device (EPID) 115 may be used to generate a set of Winston-Lutz test images (e.g., see FIGS. 3A and 3B).

Figure 3A:
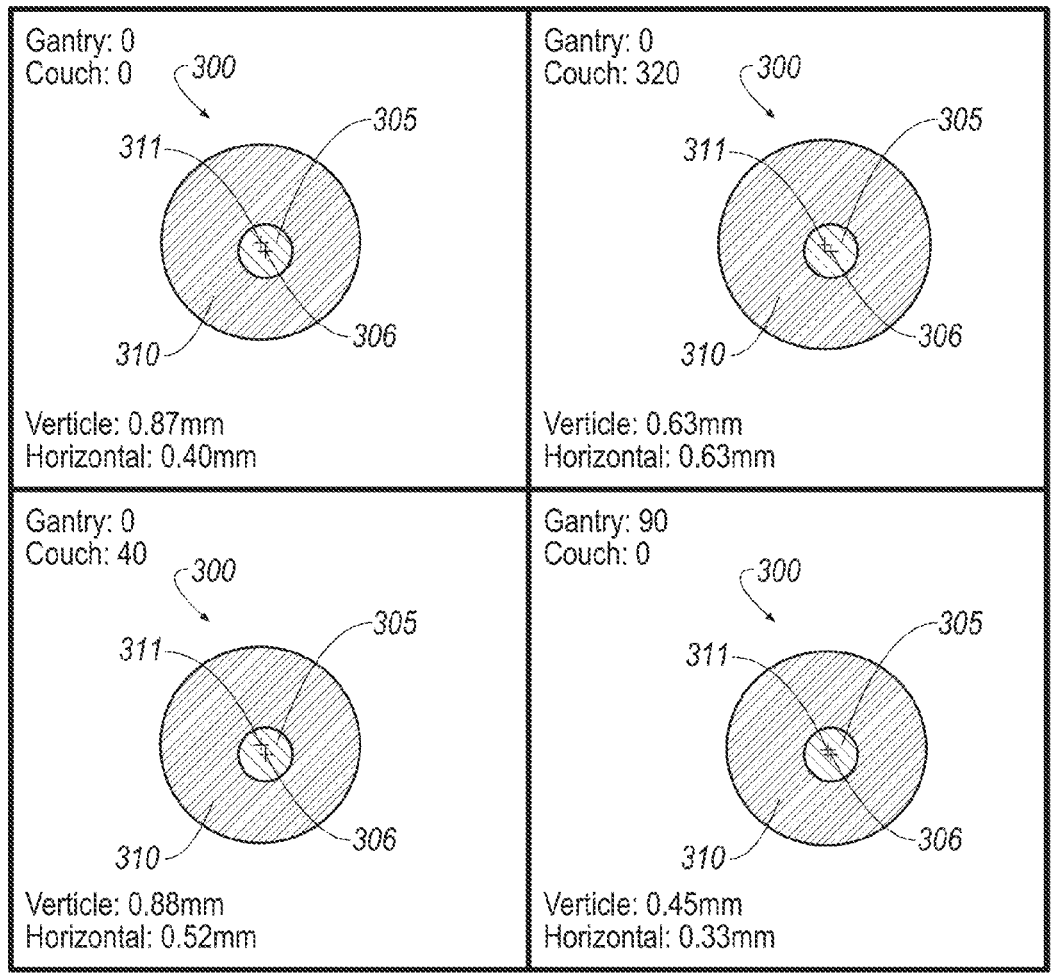
FIGS. 3A and 3B show example images from a Winston-Lutz test.
Figure 3B:
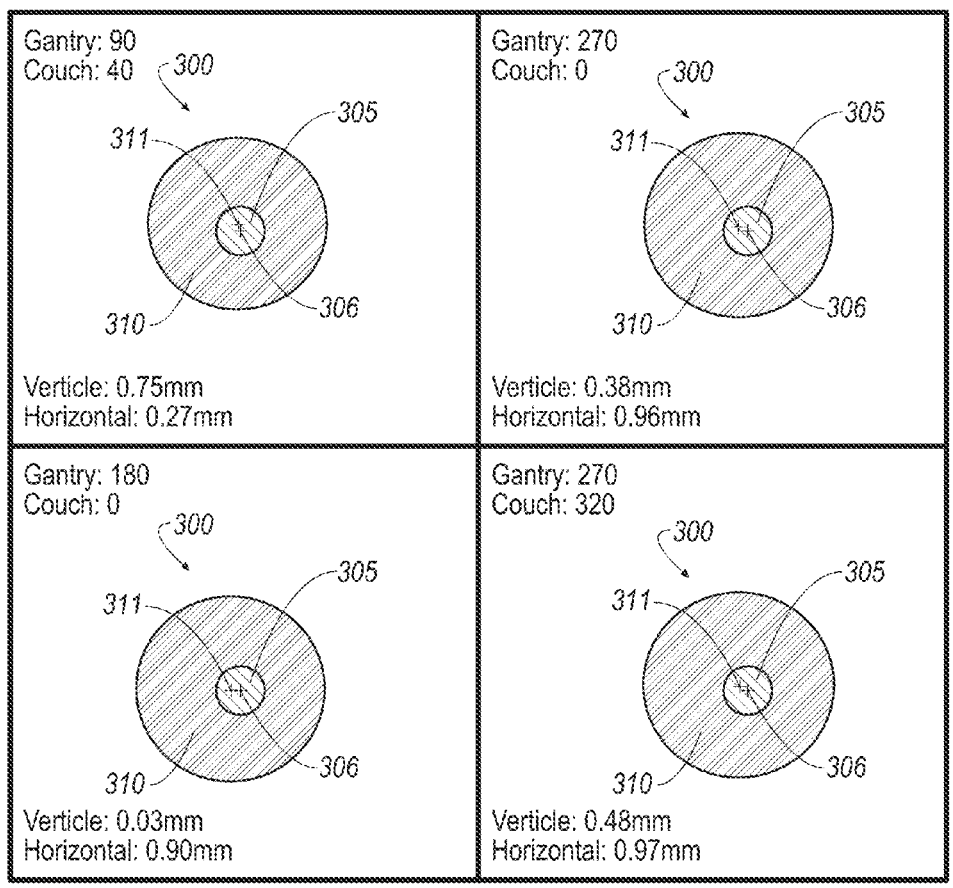

However, the Winston-Lutz images can be used at most for determining horizontal and vertical displacements, at specified angles of rotation of one or more of a gantry, couch, radiation delivery mechanism such as a collimator, etc., between a center of a test ball 114 image 305 and a center of a beam 111 image 310 (see FIGS. 3A, 3B). Thus, Winston-Lutz images 300 disadvantageously lack information about a deviation of the beam 111 radiation centers 311 from one another, but do provide data relating to mechanical and radiation isocenters at various angles of rotation of one or more of a gantry, couch, radiation delivery mechanism such as a collimator, etc. Accordingly, the computer 105 advantageously may be further programmed to use data from a Winston-Lutz test to generate a synthetic star shot that indicates a radiation isocenter and a deviation of beams 111 from the radiation isocenter at various angles of rotation of system 100 components such as the patient couch (or bed) 120, the gantry 125, and/or the collimator 130. For example, a synthetic star shot may be generated that allows for determination of a circle 410 (see FIGS. 4A, 4B, and 4C), including a distance of a radius thereof, that is a smallest circle intersecting or including at least one point of each beam 111, i.e., at each angle or combination of angles of gantry 125, couch 120, collimator 130, etc., in a Winston-Lutz test. A radius of such a circle 410 may be compared to an acceptable tolerance for a distance of beam 111 centers from a radiation isocenter to determine whether the beams 111 fall within the acceptable tolerance.

Further, traditional Winston-Lutz tests include only rotations of a gantry 125 and patient couch 120. Moreover traditional Winston-Lutz tests do not allow testing of simultaneous changes of angles of rotation of more than two of a couch 120, gantry 125, collimator 130, and/or multi-leaf collimator. The system 100 disclosed herein advantageously can generate Winston-Lutz images 300 (see FIGS. 3A and 3B) based on such simultaneous changes of angles of rotation of more than two of a couch 120, gantry 125, collimator 130, and/or multi-leaf collimator. That is, instead of, for example, holding all elements except a gantry 125 at no rotation, and rotating the gantry 125 to generate a set of Winston-Lutz images, it is now possible conduct a test in which the gantry 125, but also one or more other elements, e.g., a couch 120 and collimator 130, also rotate between one or more different exposures, from which a plurality of synthetic star shots 400 (see FIGS. 4A, 4B, and 4C) can be generated in addition to conventional Winston-Lutz images, e.g., one synthetic star shot 400 for each component of the system 100 (e.g., couch 120, gantry 125, collimator 130, etc.) being tested. Accordingly, where testing of the system 100 may have previously required up to five separate tests (gantry 125 star shot, primary collimator 130 star shot, MLC star shot, couch 120 star-shot, and conventional Winston-Lutz test) each with four to eight exposures needed, the system 100 requires just a single test with as little as six total exposures.

Yet a further advantage of the present system 100 is that the synthetic star shot 400 provides the ability to distinguish between beam 111 exposures at angles of rotation that are one-hundred and eighty degrees apart. Conventional star shots cannot make this distinction because a same piece of film is used for both exposures, and the beam 111 images tend to overlap and/or be indistinguishable. However, reconstructing digital beam center images 405 (see FIGS. 4A, 4B, and 4C) for respective beams 111 generated at angles of rotation of, e.g., a gantry 125, that are one-hundred and eighty degrees apart relies on separate exposures of the EPID 115, and on separate reconstructions of the beam center images 405 for each exposure. Thus, distinct beam center images 405, even for beams that are one-hundred and eighty degrees apart, may be represented on a synthetic star shot as disclosed herein.

System Elements

The computer 105 is a computing device included in and/or communicatively coupled to the radiation device 110. Further, the computer 105 in the present disclosure may in fact represent multiple computing devices performing operations ascribed herein to the computer 105, e.g., a first computer that is a controller, such as is known, of the radiation device 110, and a second computer that receives test data, generates a synthetic star shot 400, etc., as disclosed herein. Accordingly, the controller 105 includes a processor and a memory, the memory storing instructions executable by the processor, for performing operations described herein. The controller 105 is further communicatively coupled to the EPID 115 to receive image data and the like generated by the radiation beam 111 striking the EPID 115. Devices described herein as "communicatively coupled" should be understood to be in communication with each other via any suitable known mechanisms, e.g., a local area network, cables, wireless communications, etc.

The radiation device 110 may be a linear accelerator, a Cobalt-60 unit, a Radiation Therapy simulator etc., e.g., the device 110 is generally a known mechanism for delivering radiation to a patient. As such, the device 110 typically includes a gantry 125. The gantry 125 may have two axes of rotation, e.g., the gantry 125 may be capable of horizontal and vertical rotation. According to the exemplary three-dimensional coordinate system shown in FIGS. 2A-2F, therefore, the gantry 125 has an axis of rotation along the X-axis (vertical rotation), where for purposes of this disclosure the gantry is said to be at zero degrees vertical rotation when it is rotated zero degrees with respect to the Z-axis. As mentioned above, and as is known, the radiation device 110 provides a radiation beam 111.

As also mentioned above, the system 100 further includes a conventional Winston-Lutz apparatus 112. The apparatus 112 may be mounted at an end of the patient couch 120 in a conventional manner. Further, as is known, the Winston-Lutz apparatus 112 generally includes a test object such as a ball 114. Images 300 from a Winston-Lutz test (see FIGS. 3A, 3B) will show both a test ball 114 image 305, as well as a radiation cone image 310 representing the radiation beam 111. Because a center of the test ball 114 may represent a mechanical isocenter of the system 100, a difference in locations of image centers 306, 311 of the images 305, 310 represents a difference between a radiation isocenter and a mechanical isocenter of the system 100. However, as mentioned above, the Winston-Lutz test provides at most horizontal and vertical displacements, at specified angles of rotation of one or more of a gantry 125 and/or couch 120, between a center of a test ball 114 image 305 and a center of a beam 111 image 310 (see FIGS. 3A, 3B).

EPID 115 is an electronic portal imaging device such as is known for receiving a radiation beam 111 and providing an image thereof. As illustrated in FIGS. 2A-2F, the beam 111 generally strikes the END 115 at a pre-determined angle (a perpendicular angle, generally the simplest angle to use, is referenced herein for ease of illustration). That is, when the gantry 125 rotates as described herein, the EPID, included on a stationary platform 116 extending from a bottom portion of the gantry 116, rotates with the gantry 125. Thus, the beam 111 strikes the EPID 115 at a consistent pre-determined angle, e.g., a perpendicular angle, at any angle of rotation of the gantry 125. The END 115 may be used to generate various images in a test of the radiation device 100, such as images 300 from a Winston-Lutz test. The EPID 115 is described herein by way of an example, and not limitation, of an image capture device that could be used in the system 100 and for carrying out steps disclosed herein. Other images capture devices could be used, e.g., two-dimensional flat-panel detector arrays and/or other devices that are external to the radiation device 110, e.g., 2D and 3D diode arrays, video capture devices imaging phosphorescent screens or plates, Computed Radiography (CR) plates, Digital Radiography (DR) plates, small ion chamber arrays, etc.

The patient couch 120 is a conventional patient couch or bed for use in radiation therapy. In the context of the system 100, the patient couch 120 generally has one horizontal axis of rotation, that axis being for purposes of this disclosure the Z-axis illustrated in the drawings, the couch 120 being said to be at zero degrees when a longitudinal axis C through a center of the couch 120 is aligned with or substantially parallel to the X-axis. The couch 120 may alternatively or additionally have vertical axes of rotation (X-axis and/or Y-axis).

The collimator 130 is generally known. In the system 100, the collimator 130 may rotate about the vertical axis, e.g., the Z-axis shown in the figures. Further, although the figures show only the primary collimator 130, it is also possible, and often likely, that the radiation delivery device 110 will include a multi-leaf collimator (MLC) as well. As an alternative or in addition to performing analyses with respect to rotating the primary collimator 130 as described herein, it should be understood that like analyses may be performed with respect to an MLC.

Figure 2A:
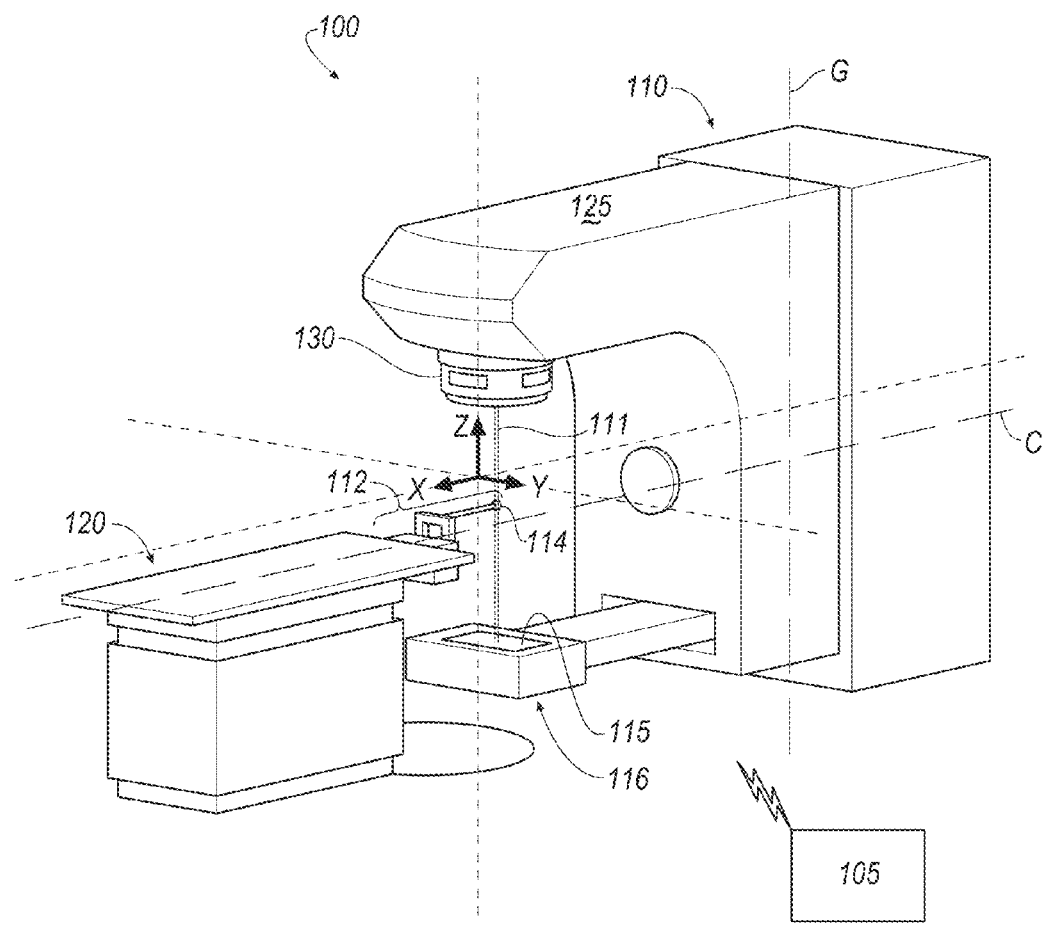
FIG. 2A is a perspective view of certain elements of the example radiation delivery system of FIG. 1, including a gantry element oriented zero degrees with respect to a vertical axis of a selected coordinate system, and a couch element oriented zero degrees with respect to a horizontal axis.
Figure 2B:
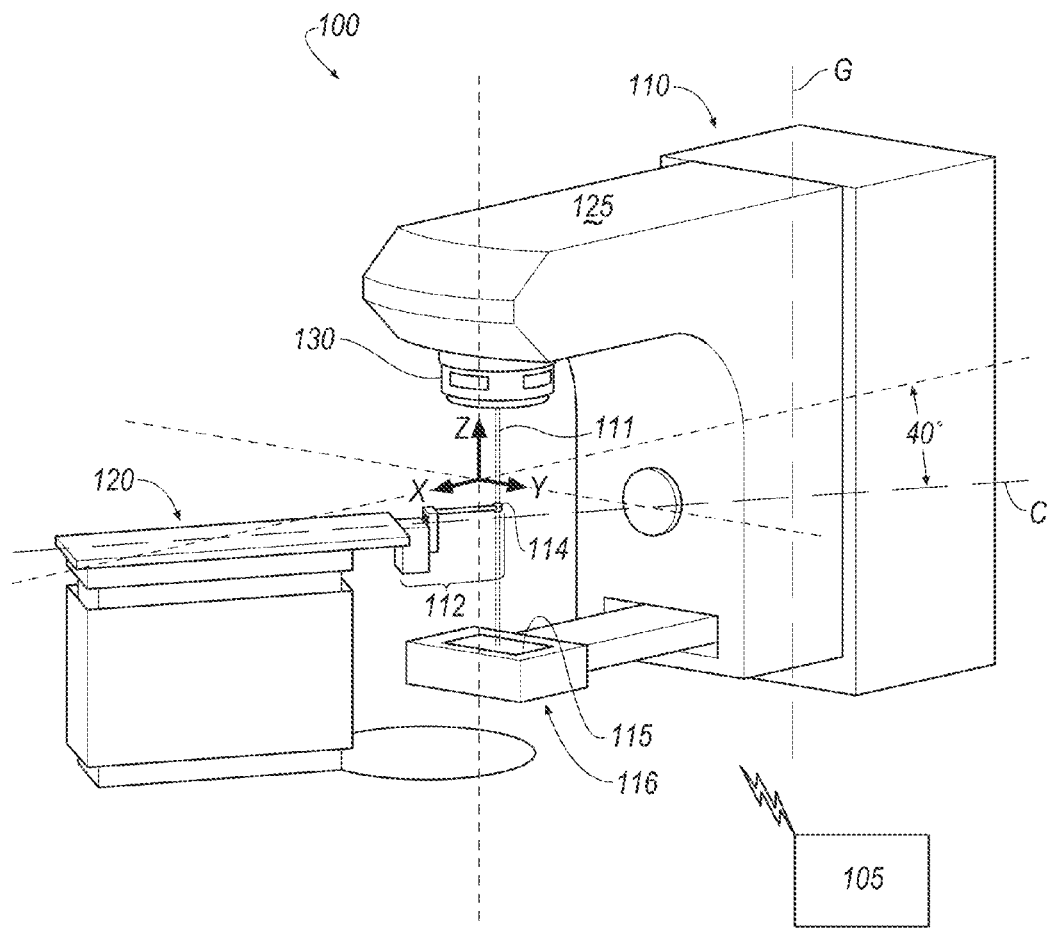
FIG. 2B is the another perspective view of the example radiation delivery system of FIG. 1, including a gantry element oriented zero degrees with respect to a vertical axis of the selected coordinate system, and a couch element oriented forty degrees with respect to a horizontal axis.
Figure 2C:
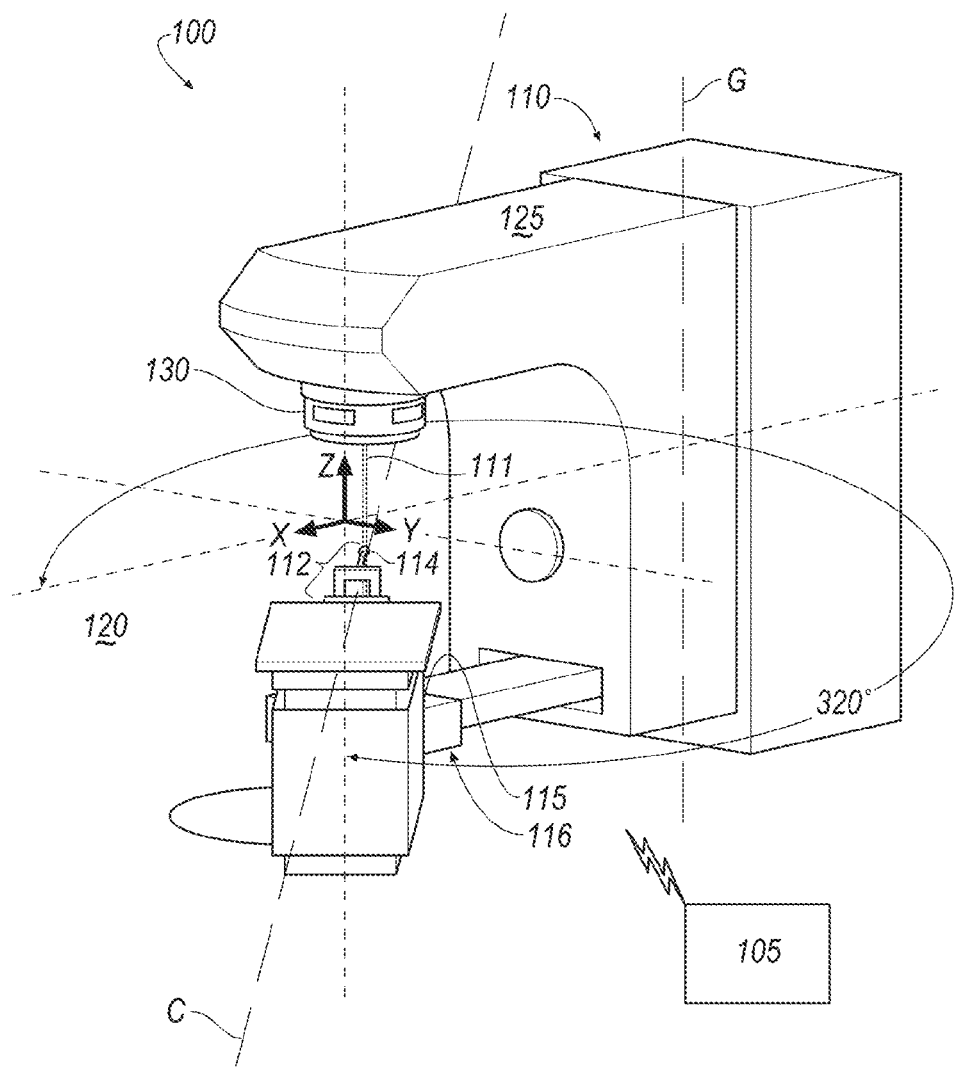
FIG. 2C is the another perspective view of the example radiation delivery system of FIG. 1, including a gantry element oriented zero degrees with respect to a vertical axis of the selected coordinate system, and a couch element oriented three hundred and twenty degrees with respect to a horizontal axis.
Figure 2D:
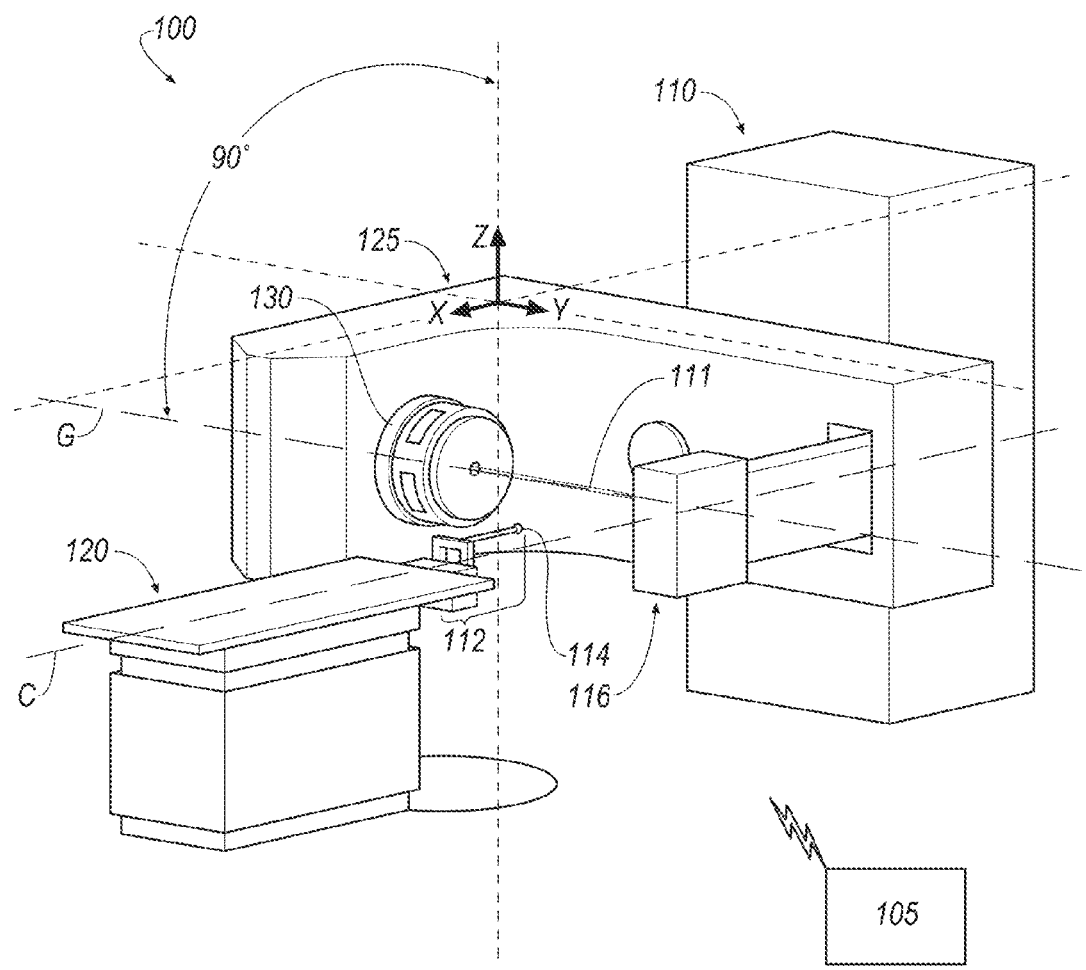
FIG. 2D is the another perspective view of the example radiation delivery system of FIG. 1, including a gantry element oriented ninety degrees with respect to a vertical axis of the selected coordinate system, and a couch element oriented zero degrees with respect to a horizontal axis.
Figure 2E:
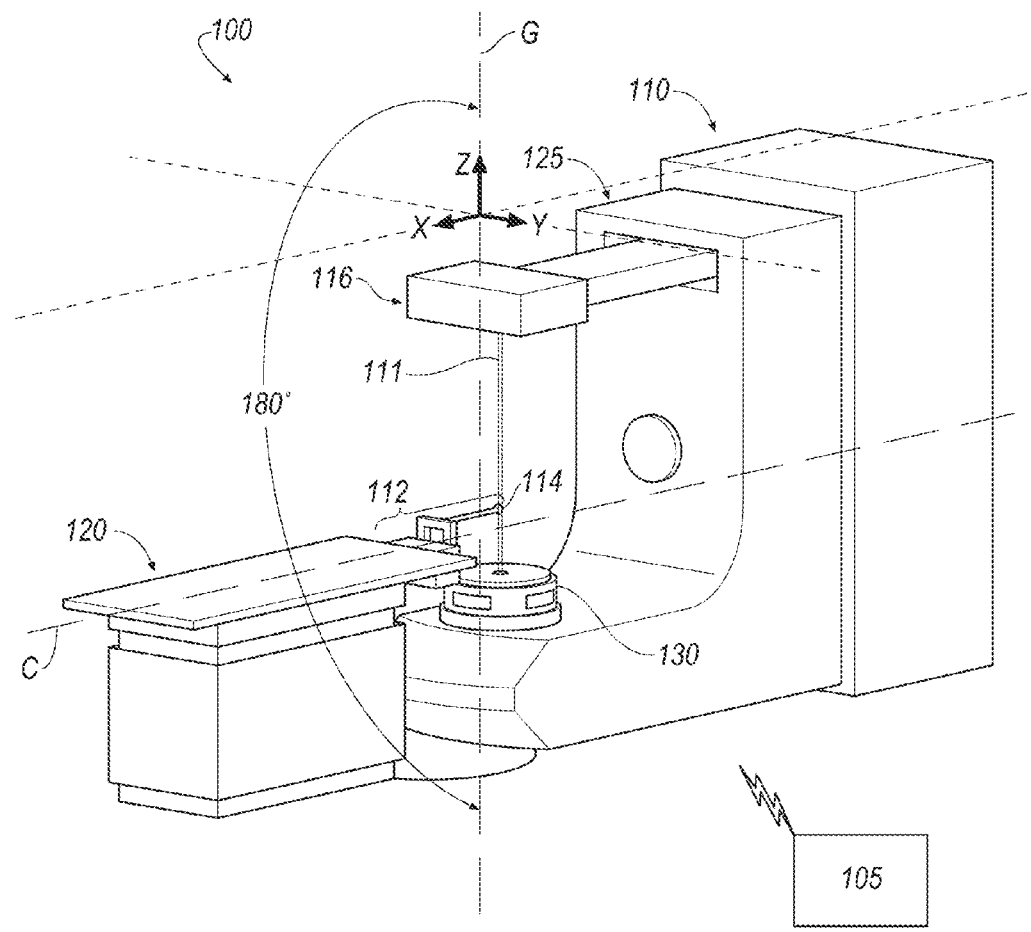
FIG. 2E is the another perspective view of the example radiation delivery system of FIG. 1, including a gantry element oriented one hundred and eighty degrees with respect to a vertical axis of the selected coordinate system, and a couch element oriented zero degrees with respect to a horizontal axis.
Figure 2F:
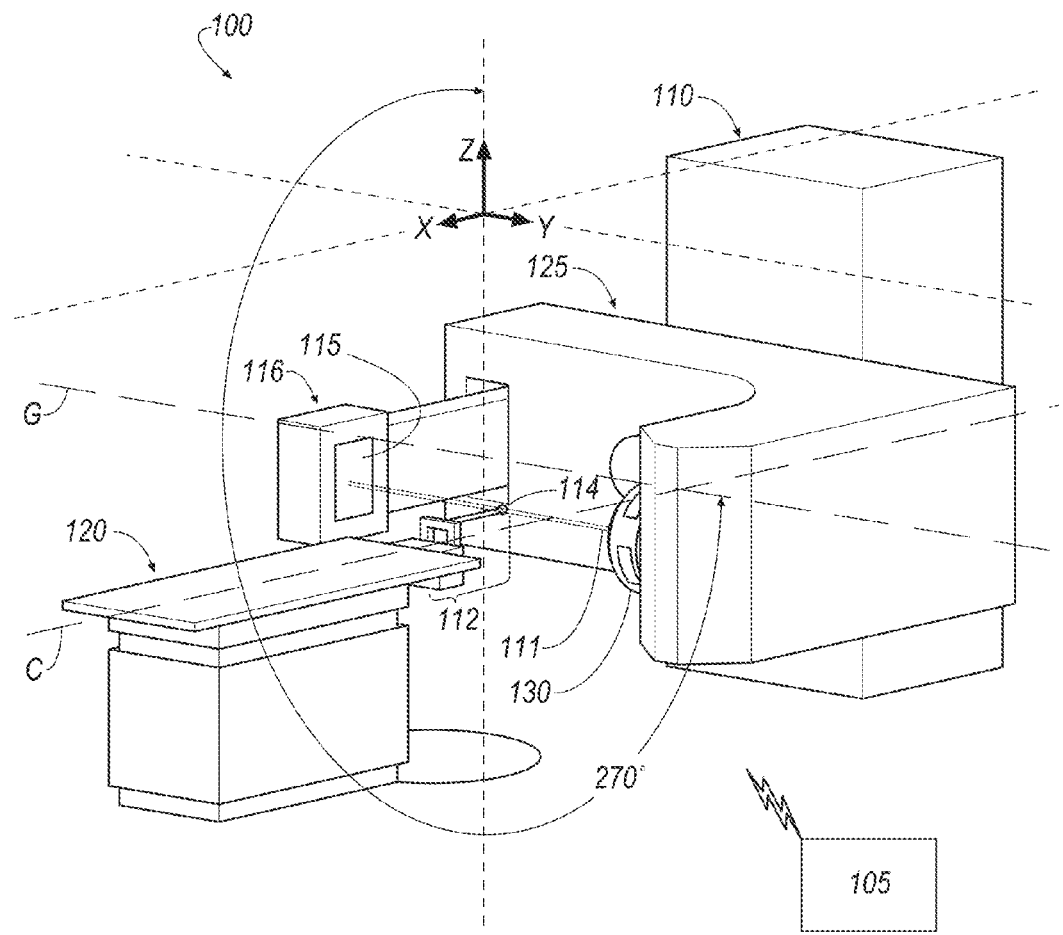
FIG. 2F is the another perspective view of the example radiation delivery system of FIG. 1, including a gantry element oriented two hundred and seventy degrees with respect to a vertical axis of the selected coordinate system, and a couch element oriented zero degrees with respect to a horizontal axis.

FIGS. 2A-2F show the system 100 with the gantry 110 and the couch 120 at various angles of rotation. For example, as best seen in FIG. 2A-2C, the couch 120 rotates about the Z-axis such that a plane defined by a surface of the EPID 115 maintains a constant angle with respect to the XY plane (i.e., a horizontal plane) in the XYZ coordinate system, but rotates through various angles with respect to the XZ plane, as measured from the X-axis. Further for example, as best seen in FIGS. 2D-2F, the gantry 110 rotates about the X-axis such that a plane defined by a surface of the EPID 115 maintains a constant angle with respect to the ZY plane in the XYZ coordinate system, but rotates through various angles with respect to the XZ plane, as measured from the Z-axis.

Figure 4A:
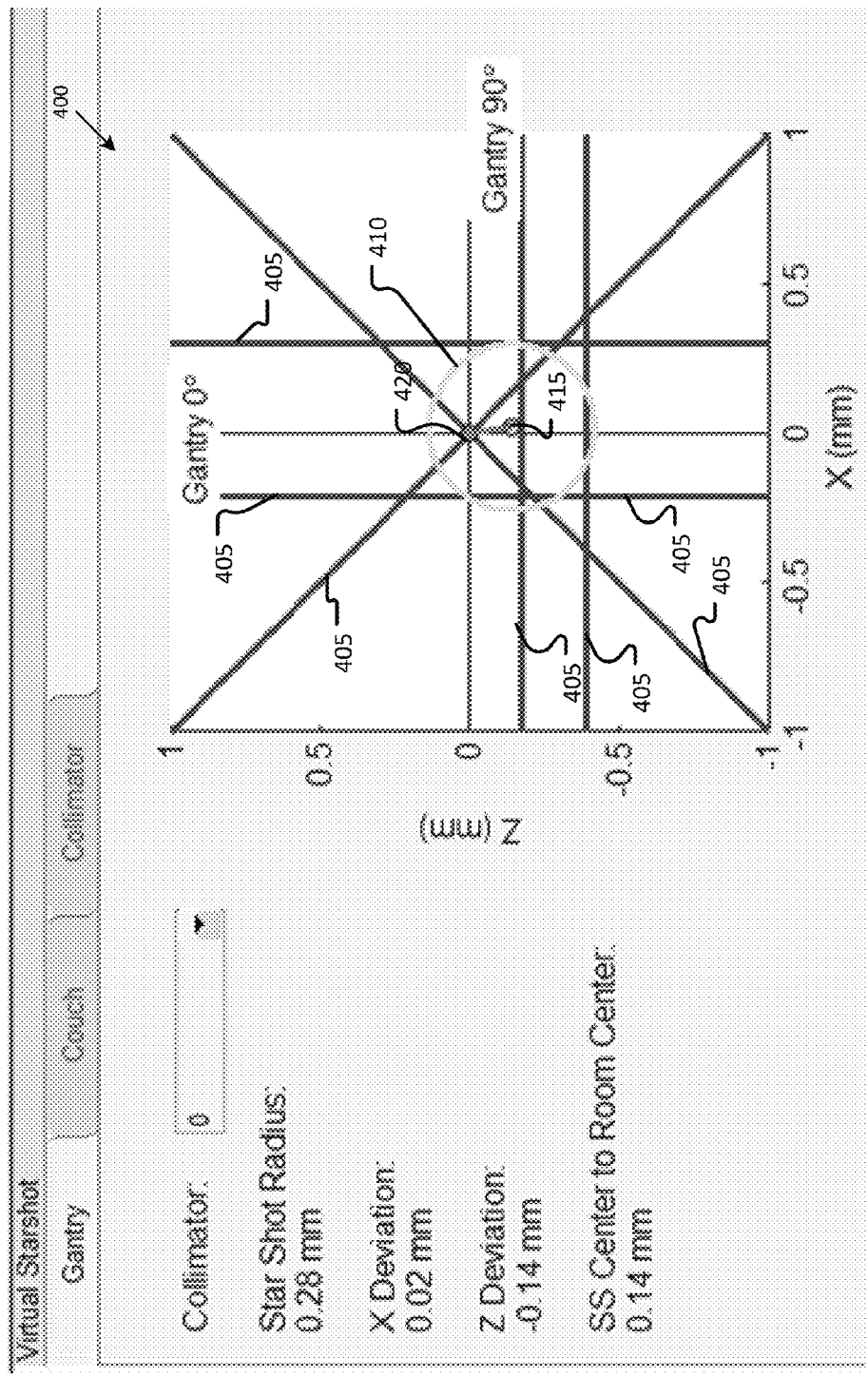
FIGS. 4A, 4B, and 4C show example synthetic star shot analysis images.
Figure 4B:
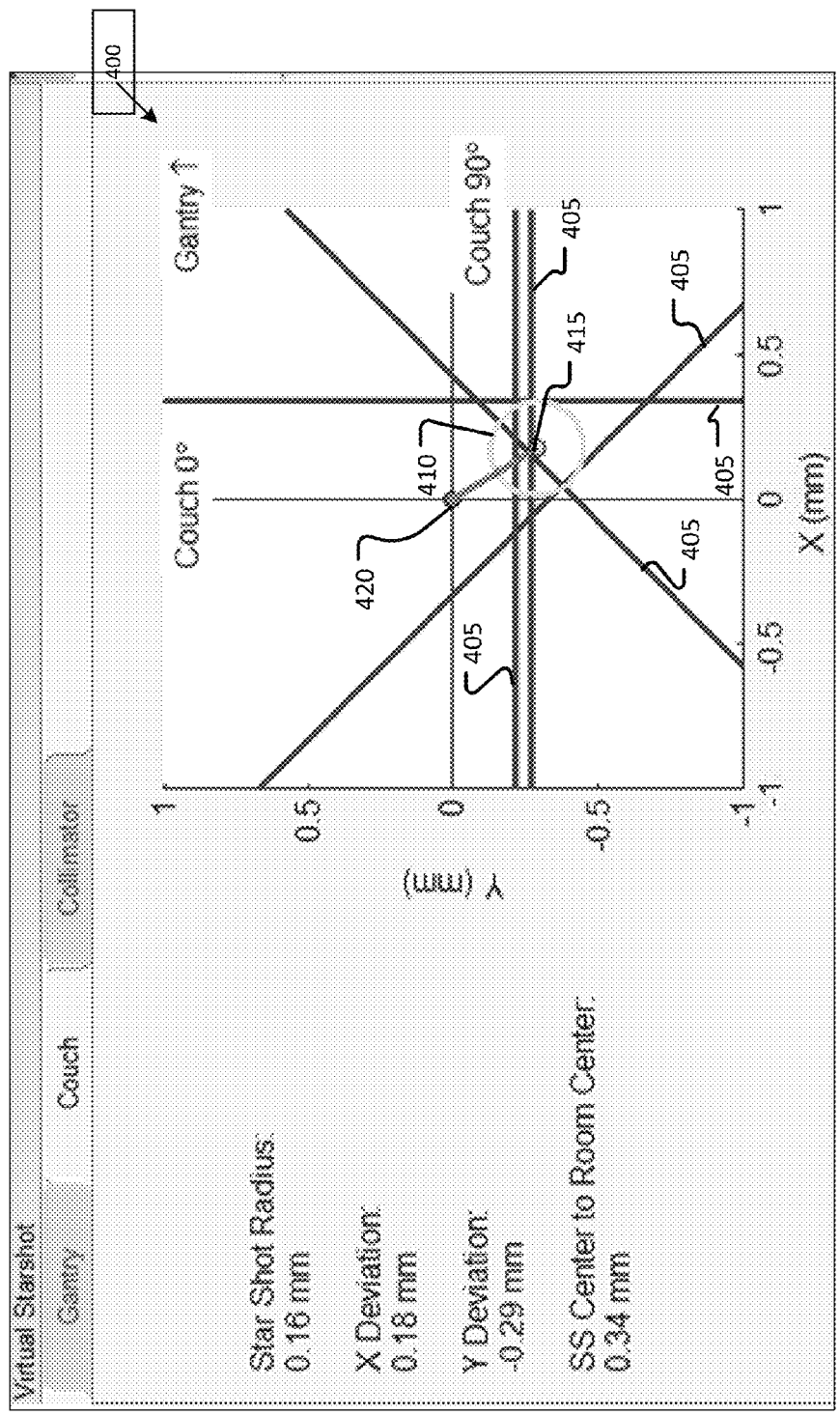
Figure 4C:
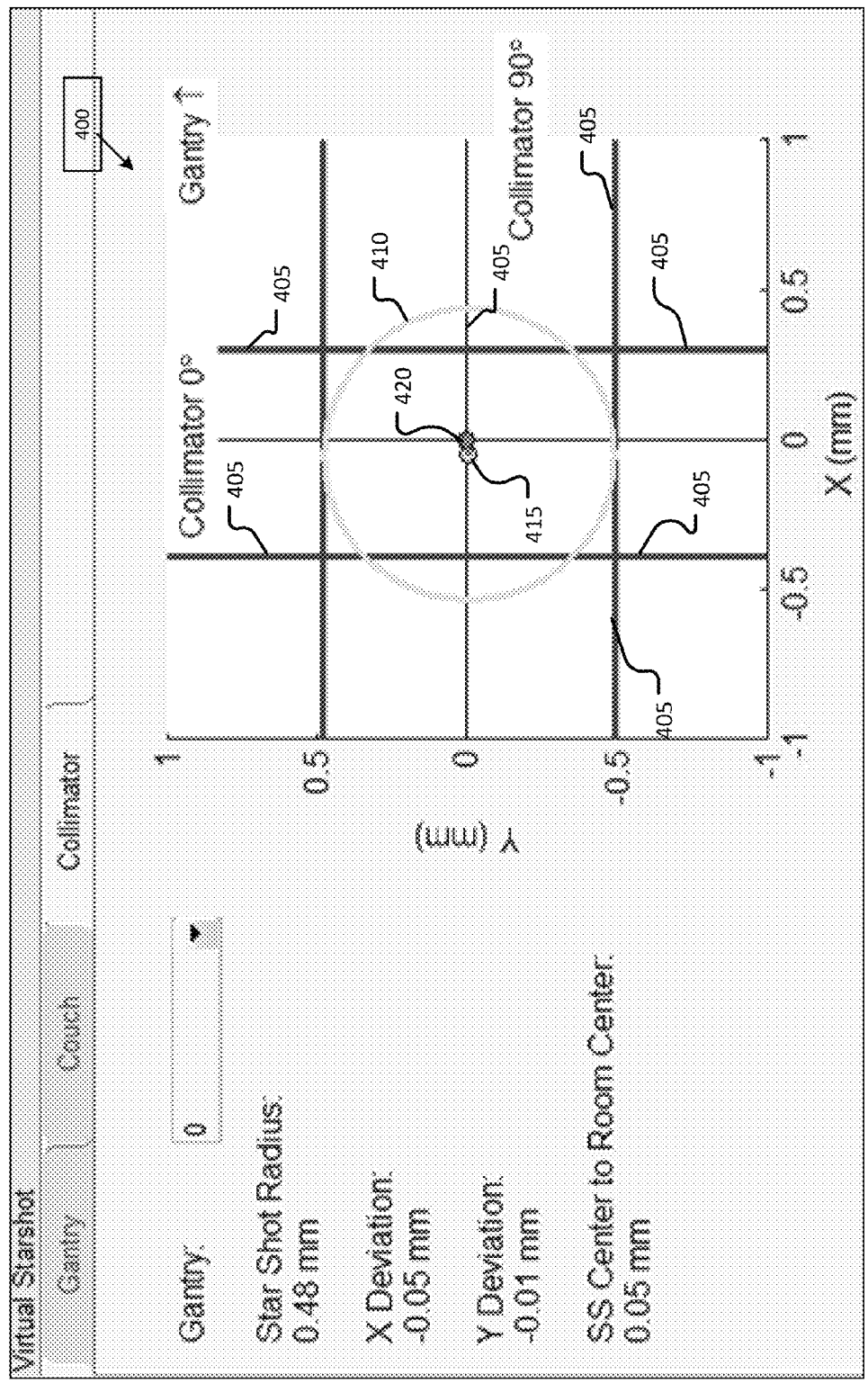

Image data captured by directing the beam 111 toward the Winston-Lutz apparatus 112 and the EPID 115 at various angles of rotation may be used by the computer 105 to obtain Winston-Lutz images such as shown in FIGS. 3A and 3B. The Winston-Lutz images may then be used to generate synthetic star shots 400 as shown in FIGS. 4A, 4B, and 4C, a process for generating a star shot image being described below with respect to FIG. 5. In particular, FIG. 4A illustrates a star shot image 400 generated by rotation of a gantry 125. FIG. 4B illustrates a star shot image 400 generated by rotation of a couch 120.

Synthetic Star Shots

A star shot image 400 includes a plurality of beam center images 405 representing beam centers at various angles of the gantry 125, couch 120, etc. (i.e., as will be understood, a beam 111 generally has a width, but the star shot 400 represents the beam 111 with a line drawn at a reconstruction of locations of the beam 111 center). For example, in FIG. 4A, the star shot 400 includes beam center images 405 representing various angles of rotation of a gantry 125, other elements, including the couch 120 and collimator 130 held at zero degrees rotation or movement. In FIG. 4B, the star shot 400 includes beam center images 405 representing various angles of rotation of a couch 120, other elements, including the gantry 125 and collimator 130 held at zero degrees rotation or movement. In FIG. 4B, the star shot 400 includes beam center images 405 representing various angles of rotation of a collimator 130, other elements, including the gantry 125 and couch 120 held at zero degrees rotation or movement.

Note that, for ease of illustration and description, although the present example images 400 are based on Winston-Lutz tests moving only one of the gantry 125, couch 120, and collimator 130 (and any other element such as an MLC), the present disclosure is not necessarily limited to such examples, and could encompass scenarios in which angles of rotation of multiple different components, e.g., a couch 120 and gantry 125, were greater than zero with respect to respective axes of rotation. For example, drop-down menu boxes 450 can be seen in FIGS. 4A and 4C. The drop-down menu 450 of FIG. 4A, presenting a synthetic star shot 400 for a gantry 125, shows a value of zero for a "collimator," but could include other angles of rotation, e.g., 90 degrees, 180 degrees, 270 degrees, etc., for the collimator 130. Likewise, the drop-down menu 450 of FIG. 4C, presenting a synthetic star shot 400 for a gantry collimator 130, shows a value of zero for a "gantry," but could include other angles of rotation, e.g., 90 degrees, 180 degrees, 270 degrees, etc., for the gantry 130.

There is no similar drop-down menu 450 on the FIG. 4B, because, in the presently-described exemplary implementation, for the couch 420 there is no need to select angles of other components. The couch 120 typically rotates completely independently of the gantry 125 and collimator 130. Therefore, rotations of the gantry 125 and collimator 130 do not affect the rotational accuracy of the couch 120. However, the gantry 125 and collimator 130 are physically connected (as can be seen in FIGS. 2A-2F), and as such, it is useful to determine the rotational accuracy of the collimator 130 at various gantry 125 rotations and visa-versa. It is typically not useful, nor does it make physical sense, to test the rotational accuracy of the couch 120 at various gantry 125 or collimator 130 rotations, because the effect will be the same at all rotations, and rotating either one would simply serve to add uncertainty to measurements being made.

Therefore, it is not necessary to specify gantry 125 or collimator 130 angle with couch 120 star shots 400, and accordingly a gantry 125 angle of zero is presently recommended to generate a synthetic star shot 400 for the couch 120. However, as a general proposition, it is possible that a synthetic star shot 400 screen for the couch 120 could show a "collimator" drop-down menu. For the present exemplary implementation, as just explained, it is assumed that an angle of the collimator 130 will not impact results indicating deviations with respect to the couch 120. On the other hand, when rotating the collimator 130, the present exemplary implementation takes into account an angle of the gantry 125 because the gantry 125 position can be relevant to effects of gravity on collimator 130 leaves (e.g., at 90 and 270 degree rotations where the leaves have to fight gravity the most).

Returning to FIGS. 4A, 4B, and 4C, the beam center images 405 can be used to construct a circle 410 having a center 415 that represents a radiation isocenter. For example, the circle 410 could be defined according a smallest circle that can be drawn intersecting and/or containing at least one point of each of the beam images 405. Further, a mechanical isocenter image 420 may also be provided, the mechanical isocenter being at the intersection of coordinate axes as described above. Accordingly, the star shot 400 may advantageously show on one image, as was not previously possible absent an error-prone manual step such as making a pin-prick on a sheet of film, a distance of mechanical and radiation isocenters, in addition to showing a deviation of beams 111 (represented by beam center images 405) from the radiation isocenter. Thus, as described above, the beam center images 405 may be used to determine whether the beams 111 are all within an acceptable tolerance, i.e., distance, of the radiation isocenter. Further, it should be understood that the circle 410, and other indicia, e.g., indicia relating to a mechanical isocenter and/or radiation isocenter and/or a distance therebetween are not, strictly speaking, part of a star shot inasmuch as, strictly speaking, beam 111 images 405 make up the star shot, and other items are added as part of analysis of the star shot 400. However, for convenience, a synthetic star shot 400 may also be understood to include a circle 410, centers 415, 420, etc.

Process Flow

Figure 5:
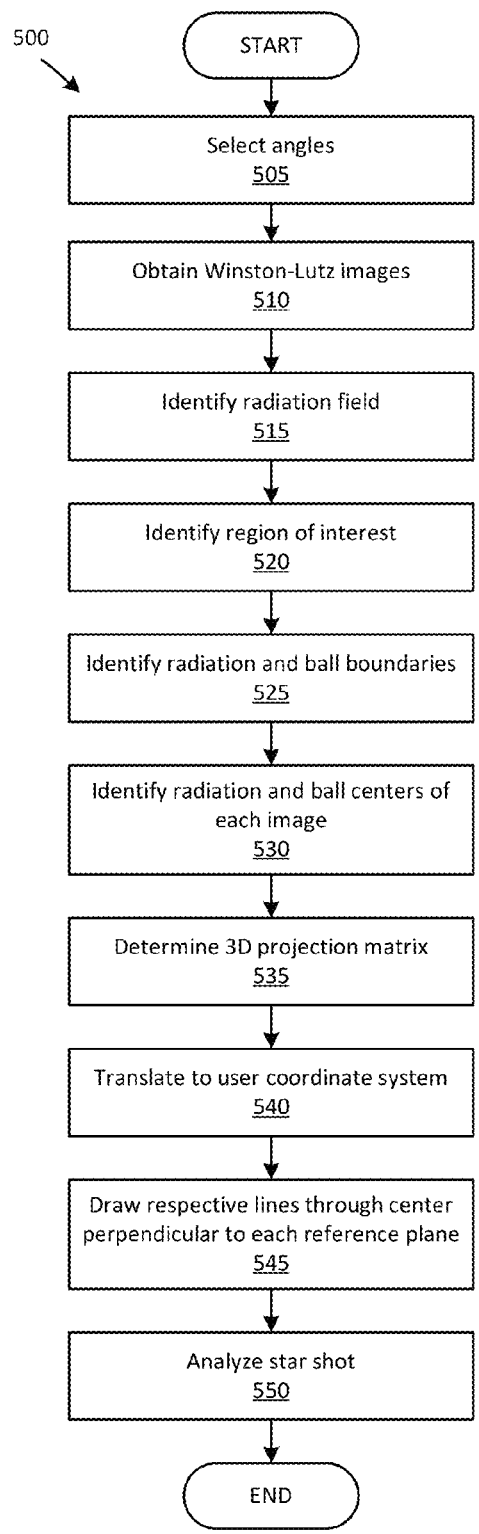
FIG. 5 illustrates an example process for generating a synthetic star shot.

FIG. 5 illustrates an exemplary process 500 for generating a synthetic star shot 400. The process 500 begins in a block 505, in which the computer 105 receives input specifying a set of angles of rotation for one or more of the gantry 125, couch 120, and collimator 130. As noted above, typically, but not necessarily, only one component of the system 100 will be rotated to generate an image 400.

Next, in a block 510, the radiation delivery device 110, generally including the gantry 125, the collimator 130, and/or the couch 120, e.g., are controlled and used in a manner known for a Winston-Lutz test to obtain Winston-Lutz images 300, e.g., as shown in FIGS. 3A and 3B.

Next, in a block 515, a radiation field in each of the Winston-Lutz images 300 is identified. In general, as is known, a radiation field in a Winston-Lutz image 300 is identified with a region of the image showing radiation e.g., a beam 111 image 310. As is known, the radiation field, e.g., image 310, may be circular, generally square or rectangular, etc. In any case, such radiation field is sometimes generally referred to as the "cone," as mentioned above.

Next, in a block 520, a region of interest in each Winston-Lutz image 300 is identified according to the cone or radiation field identified in each of the Winston-Lutz images 300. That is, an image 300 may be cropped to include substantially only a cone or beam 111 image 310, which generally encompasses a ball 114 image 105.

Next, in a block 525, radiation field and ball centers are identified for each of the Winston-Lutz images 300, e.g., centers 306, 311, of the ball 114 image 305 and beam 111 image 310.

Next, in a block 530, mechanical isocenters 307, and beam centers 311, are respectively defined for each of the Winston-Lutz images 300 obtained in the block 510. As noted above, the Winston-Lutz images 300 disadvantageously lack information about a deviation of the beam 111 radiation centers 311 from one another, but do provide data relating to mechanical and radiation isocenters.

Next, in a block 535, for each of the Winston-Lutz images 300 obtained in the block 510, a three-dimensional (3-D) projection matrix may be determined. That is, an XYZ coordinate system may be determined wherein horizontal axes lie on a plane defined by the two-dimensional image 300, and a vertical axis extends perpendicular to the horizontal or image 300 plane. The plane defined by each image 300 may be referred to as a "reference plane." The reference plane is defined, for each image 300, according to the angle of rotation of the gantry 125, collimator 130, and/or couch 120, etc., when the beam center image 311 was made.

Next, in a block 540, the 3-D projection matrix, i.e., three-dimensional base coordinate system, is translated to a user coordinate system. The block 540 is optional, but, as will be understood, different radiation delivery devices 110 may specify different coordinate systems for delivering radiation. Accordingly, the block 540 performs a translation to allow for providing results in a coordinate system used by the radiation delivery device 110 by which a test was conducted. Such translation may be done in a generally known manner. In one example, signs, may need to be reversed (e.g., a specification of forty degrees from the X-axis becomes negative forty degrees, etc.), or other adjustments made to a specification of an angle, or a distance, may need to be made.

Next, in a block 545, for each of the Winston-Lutz images 300 obtained in the block 510, the controller 105 identifies a line perpendicular to the plane defined by a surface of the EPID 115 when the image 300 was made, i.e., perpendicular to the Winston-Lutz image, the line being drawn through the beam center 311 for the image 300. (As mentioned above, a radiation beam 111 could be provided at an angle other than perpendicular to a horizontal plane including a Winston-Lutz ball 114, in which case a line at the angle other than perpendicular may be identified in this block 545.) Three examples of synthetic star shots 400 that can be reconstructed include the following:

1) A gantry 125 star shot 400 could use beam 111 projections, e.g., beam center images 405, in the YZ plane such as shown in FIGS. 2A-2F where Y is a horizontal component and Z is a vertical component with respect to the gantry 125. In one non-limiting implementation, the star shot 400 reconstructs such beam 111 images 405 only for exposures of the EPID 115 where the couch 120 and collimator 130 angles are zero as described above, i.e., couch 120 and collimator 130 have not been rotated. However, as noted above, examples are possible where couch 120 and collimator 130 have not been rotated.

2) A couch star shot 400 could use beam 111 projections, e.g., beam center images 405, in the XY plane, where Y is a horizontal component and X is a vertical component with respect to the couch 120. Note that, in reconstructing, i.e., generating, a couch 120 star shot 400, signs for specified angles may be reversed for each projection value in the block 510 described above, i.e., each plot of a beam center image 405 in the star shot 400. The reason for this is that, by default a Winston-Lutz test would typically measure a displacement of a mechanical isocenter 410 and a radiation isocenter 415 by calculating mechanical isocenter 410 minus radiation isocenter 415. However, for a couch 120 star shot, the calculation of interest is radiation isocenter 415 minus mechanical isocenter 410. In one non-limiting implementation, the star shot 400 reconstructs such beam 111 images 405 only for exposures of the EPID 115 where the gantry 125 and collimator 130 angles are zero as described above, i.e., gantry 125 and collimator 130 have not been rotated. However, as noted above, examples are possible where couch 120 and collimator 130 have not been rotated.

3) A collimator 130 star shot 400 could use beam 111, e.g., beam center images 405, projections in the XY plane, where Y is a horizontal component and X is a vertical component with respect to the collimator 130. In one non-limiting implementation, the star shot 400 reconstructs such beam 111 images 405 only for exposures of the EPID 115 where the gantry 125 and couch 120 angles are zero as described above, i.e., gantry 125 and couch 120 have not been rotated. However, as noted above, examples are possible where couch 120 and gantry 125 have not been rotated.

Next, in a block 550, the controller 105 analyzes the synthetic star shot 400. For example, a determination of a deviation from a radiation isocenter may be represented in a number of ways, e.g., by a small as possible circle 410 through and/or enclosing at least one point on each of the beam center lines 405, etc. Other data may be indicated, such as a mechanical isocenter 420 (previously locatable on a star shot only by error-prone manual placement), a distance between mechanical and radiation isocenters 415, 420, etc. Other examples of determining a deviation from a radiation isocenter are, without limitation, determining the edge intersection of a circle as defined in ANSI N449.1, the furthest beam intersection distance, maximum perpendicular distance to a user defined center, and distance from mechanical isocenter to center-of-gravity of beam intersection points among other known techniques.

Following the block 550, the process 500 ends.

Computing devices such as those discussed herein generally each include instructions executable by one or more computing devices such as those identified above, and for carrying out blocks or steps of processes described above. Computer-executable instructions may be compiled or interpreted from computer programs created using a variety of programming languages and/or technologies, including, without limitation, and either alone or in combination, Java™, C++, Visual Basic, Java Script, Perl, HTML, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media. A file in a computing device is generally a collection of data stored on a computer readable medium, such as a storage medium, a random access memory, etc.

A computer-readable medium includes any medium that participates in providing data (e.g., instructions), which may be read by a computer. Such a medium may take many forms, including, but not limited to, non-volatile media, volatile media, etc. Non-volatile media include, for example, optical or magnetic disks and other persistent memory. Volatile media include dynamic random access memory (DRAM), which typically constitutes a main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

With regard to the media, processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of systems and/or processes herein are provided for the purpose of illustrating certain embodiments, and should in no way be construed so as to limit the disclosed subject matter.

Accordingly, it is to be understood that the above description is intended to be illustrative and not restrictive. Many embodiments and applications other than the examples provided would be apparent to those of skill in the art upon reading the above description. The scope of the invention should be determined, not with reference to the above description, but should instead be determined with reference to claims appended hereto and/or included in a non-provisional patent application based hereon, along with the full scope of equivalents to which such claims are entitled. It is anticipated and intended that future developments will occur in the arts discussed herein, and that the disclosed systems and methods will be incorporated into such future embodiments. In sum, it should be understood that the disclosed subject matter is capable of modification and variation.

We claim:

1. A system, comprising a computer including a processor and a memory, the memory storing instructions executable by the processor such that the computer is programmed to:
   receive a set of first images, each of the first images including respective exposures of an image capture device to a beam of radiation, each of a plurality of components of a radiation delivery system being at respective specified orientations with respect to a three-dimensional coordinate system during each of the exposures;
   reconstruct respective beam images from each of the exposures by drawing a line at a predetermined angle to the first image and through a center of a radiation beam shown on each first image; and
   combine the reconstructed beam images on a second image.

2. The system of claim 1, wherein the computer is further programmed to receive a set of angles, for at least one of the components, with respect to a plane in a coordinate system at which each of the first images is to be made.

3. The system of claim 2, wherein the computer is further programmed to cause the radiation delivery system to deliver a beam of radiation at each angle of the at least one component in the set of angles, thereby generating the respective exposures of the image capture device.

4. The system of claim 1, wherein the plurality of components includes more than one of a radiation delivery device gantry, a collimator, a multi-leaf collimator, and a patient couch.

5. The system of claim 1, wherein each of the exposures is made by moving one and only one of the components through successive angles of rotation.

6. The system of claim 1, wherein the computer is further programmed to at least one of identify a mechanical isocenter on the second image and to identify a radiation isocenter on the second image.

7. The system of claim 6, wherein the computer is further programmed to identify distances of the beams from the radiation isocenter.

8. The system of claim 1, wherein the computer is further programmed to determine a distance between mechanical isocenter on the second image and a radiation isocenter on the second image.

9. The system of claim 1, wherein each of the first images further includes a representation of a test object representing a mechanical isocenter of the radiation delivery system.

10. A radiation delivery system, comprising:
   a gantry;
   a radiation delivery mechanism affixed to the gantry;
   an image capture device affixed to the gantry and oriented to receive a beam of radiation from the radiation delivery mechanism;
   a patient couch;
   a Winston-Lutz test apparatus affixed to the patient couch, the Winston-Lutz test apparatus including a test object representing a mechanical isocenter of the radiation delivery system, the test object being positioned between the radiation delivery mechanism and the gantry; and
   a computer including a processor and a memory, the memory storing instructions executable by the processor such that the computer is programmed to:
      receive a set of first images, each of the first images including respective exposures of the Winston-Lutz test apparatus and the image capture device to a beam of radiation, each of the gantry, patient couch, and collimator being at respective specified orientations with respect to a three-dimensional coordinate system during each of the exposures;
      reconstruct respective beam images from each of the exposures by drawing a line at a predetermined angle to the first image and through a center of a radiation beam shown on each first image; and combine the reconstructed beam images on a second image.

11. The system of claim 10, wherein the computer is further programmed to identify a radiation isocenter on the second image.

12. The system of claim 11, wherein the computer is further programmed to identify distances of the beams from the radiation isocenter.

13. The system of claim 10, wherein the computer is further programmed to determine a distance between mechanical isocenter on the second image and a radiation isocenter on the second image.

14. A method, comprising:
receiving a set of first images, each of the first images including respective exposures of an image capture device to a beam of radiation, each of a plurality of components of a radiation delivery system being at respective specified orientations with respect to a three-dimensional coordinate system during each of the exposures;
reconstructing respective beam images from each of the exposures by drawing a line at a predetermined angle to the first image and through a center of a radiation beam shown on each first image; and
combining the reconstructed beam images on a second image.

15. The method of claim 14, further comprising receiving a set of angles, for at least one of the components, with respect to a plane in a coordinate system at which each of the first images is to be made.

16. The method of claim 15, further comprising causing the radiation delivery system to deliver a beam of radiation at each angle of the at least one component in the set of angles, thereby generating the respective exposures of the image capture device.

17. The method of claim 14, wherein the plurality of components includes two or more of a radiation delivery device gantry, a collimator, a multi-leaf collimator, and a patient couch.

18. The method of claim 14, wherein each of the exposures is made by moving one and only one of the components through successive angles of rotation.

19. The method of claim 14, further comprising identifying at least one of a mechanical isocenter and a radiation isocenter on the second image.

20. The method of claim 19, further comprising identifying distances of the beams from the radiation isocenter.

21. The method of claim 14, further comprising determining a distance between mechanical isocenter on the second image and a radiation isocenter on the second image.

22. The method of claim 14, wherein each of the first images further includes a representation of a test object representing a mechanical isocenter of the radiation delivery system.

* * * * *